United States Patent [19]

Nowack et al.

[11] Patent Number: 4,849,576
[45] Date of Patent: Jul. 18, 1989

[54] PRETREATMENT OF BUTENES

[75] Inventors: Gerhard P. Nowack; Marvin M. Johnson; Ted H. Cymbaluk, all of Bartlesville, Okla.

[73] Assignee: Phillips Petroleum Company, Bartlesville, Okla.

[21] Appl. No.: 198,541

[22] Filed: May 17, 1988

[51] Int. Cl.⁴ .............................................. C07C 5/23
[52] U.S. Cl. .................................... 585/670; 208/249
[58] Field of Search .......................... 585/670; 208/249

[56] References Cited

U.S. PATENT DOCUMENTS

| | | | |
|---|---|---|---|
| 3,825,503 | 7/1974 | Patrick et al. | 252/462 |
| 3,983,030 | 9/1976 | Rosynek et al. | 208/249 |
| 4,177,136 | 12/1979 | Harrington et al. | 208/215 |
| 4,293,728 | 10/1981 | Montgomery | 585/670 |

*Primary Examiner*—Curtis R. Davis
*Attorney, Agent, or Firm*—K. K. Brandes

[57] ABSTRACT

In a process for isomerizing monoolefins having a terminal double bond (in particular the isomerization of butene-1 to butene-2) in the presence of a Group VIII metal catalyst (in particular an alumina-supported Pd catalyst) which is contaminated by impurities in the monoolefin containing feed, the improvement comprises pretreating the feed with a solid material comprising tin oxide and a refractory support material (in particular alumina).

20 Claims, 1 Drawing Sheet

PRETREATMENT OF BUTENES

BACKGROUND OF THE INVENTION

In one aspect, this invention relates to a process for isomerizing monoolefins containing a terminal double bond to monoolefins containing an internal double bond. In another aspect, this invention relates tot he isomerization of a butene-1 containing feed, in the presence of a noble metal catalyst, so as to produce butene-2. In a further aspect, this invention relates to pretreating monoolefin-containing isomerization feeds so as to remove catalyst poisons therefrom.

It is known to isomerize monoolefins containing a terminal double bond, in particular butene-1, to monoolefins containing an internal double bond, in the presence of a Group VIII noble metal catalyst, in particular Pd/Al$_2$O$_3$. It is also known to pretreat monoolefin containing isomerization feeds so as to remove therefrom impurities which can adversely affect the isomerization activity of the noble metal catalyst. The instant invention provides an improved process for pretreating monoolefin isomerization feeds.

SUMMARY OF THE INVENTION

It is an object of this invention to provide an improved process for isomerizing monoolefins containing a terminal double bond to monoolefins containing an internal double bond. It is another object of this invention to provide an improved process for isomerizing butene-1 (also referred to as 1-butene) to butene-2 (also referred to as 2-butene), in the presence of a noble metal catalyst. It is a further object of this invention to pretreat a feed for a monoolefin isomerization process so as to remove catalyst poisons therefrom. Other objects and advantages will be apparent from the detailed description and the appended claims.

According to this invention, is an isomerization process wherein a feed comprising at least one isomerizable monoolefin having a terminal double bond is contacted with a catalyst composition comprising a Group VIII noble metal under such isomerization conditions as to produce at least one monoolefin having an internal double bond and wherein the performance (activity or life or both) of said catalyst composition is adversely affected by impurities contained in said feed, the improvement comprises contacting (pretreating) said feed, prior to the contacting with the Group VIII noble metal isomerization catalyst, with a pretreating material comprising at least one tin oxide and an inorganic refractory support material (preferably alumina), under such pretreating conditions as to remove at least a portion of said impurities and to enhance catalyst performance (i.e., to increase the catalyst life and the rate of the conversion of said at least one monoolefin having a terminal double bond to said at least one monoolefin having an internal double bond).

In a specific embodiment of this invention, a catalytic process for isomerizing butene-1 to butene-2 comprises the steps of:

(a) passing a feed comprising butene-1 and impurities (in particular sulfur impurities), which can adversely affect the performance activity and/or life of the catalyst composition used in step (b), through a zone containing a solid pretreating material comprising at least one tin oxide and alumina, under such pretreating conditions as to remove at least a portion of said impurities and to enhance the performance of the catalyst composition; and (b) contacting the effluent from step (a) with a catalyst composition comprising a Group VIII noble metal (in particular palladium) under such isomerization condition as to convert at least a portion of butene-1 contained in said feed to butene-2.

DETAILED DESCRIPTION OF THE INVENTION

Figure 1:
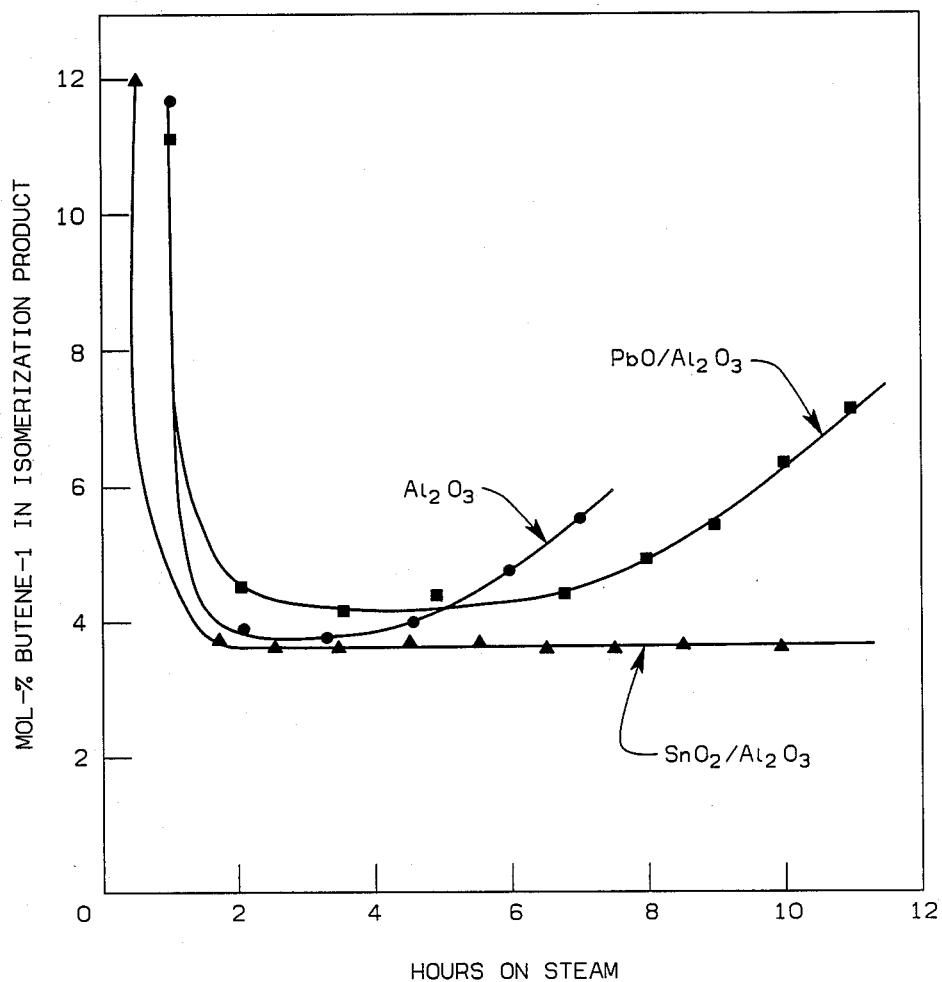
FIG. 1 illustrates the effect of various materials used in the pretreating step of this invention on the conversion of butene-1 (more specifically the amount of unconverted butene-1) in the subsequent isomerization process employing a palladium catalyst.

The pretreating step of this invention can be carried out with any feed which contains at least one isomerizable monoolefin (i.e., one monooflin or two monoolefins or more than two monoolefins) having a terminal double bond (i.e., a carbon-carbon double between the last two carbon atoms in a hydrocarbon chain) which can be shifted within the monoolefin molecule without skeletal change. Non-limiting examples of monoolefins (preferably containing 4–12 C atoms per molecule) are butene-1, n-pentene-1, 3-methylpentene-1, n-hexene-1, 4-methylhexene-1, n-heptene-1, n-octene-1, 5-methyloctene-1, and the like, and mixtures thereof. The presently preferred monoolefin is butene-1. The feed can comprise additional components such as normal alkanes, isoalkanes, monoolefins with internal double bonds (e.g., butene-2, pentene-2, hexene-3), aromatic hydrocarbons and the like, as long as these components do not adversely affect the double-bond isomerization of the isomerizable monoolefin contained in the feed. The feed can be gaseous or liquid.

The feed further comprises substances (impurities) which can act as poisons for the catalyst used in the isomerization step. Impurities in the feed frequently are elemental sulfur and/or sulfur compounds, such as hydrogen sulfide, mercaptans (such as aliphatic mercaptans, e.g., ethyl mercaptan), organic sulfides (such as diethyle sulfide and the like), organic disulfides (such as diethyl disulfide) and the like, carbonyl sulfide, sulfur oxides, and mixtures thereof. It is believed that these sulfur impurities are the primary catalyst posions, in accordance with the disclosure of U.S. Pat. No. 4,293,728, herein incorporated by reference. Other compounds which can also be present and are believed to be catalyst poisons are arsine, alkyl-substituted arsines, nitrogen oxides, free halogens, and the like. Generally the level of impurities in the feed is in the range of from about 1 to about 1,000 ppmw (parts by weight of impurity substance per million parts by weight of feed)

The solid composition employed in the pretreating step comprises (preferably consists essentially of) an inorganic refractory material, preferably alumina, and a tin oxide, i.e., SnO or SnO$_2$ (preferred) or a mixture of SnO and Sno$_2$. Other, less preferred inorganic refractory materals include silica, alumina-silica, titania, alumina-titania, aluminum phosphate, phosphated alumina (comprising Al$_2$O$_3$ and AlPO$_4$), and the like. Generally the weight percentage of the tin oxide in the solid pretreating composition is in the range of from about 1 to about 50, preferably from about 2 to about 20 weight-%, tin oxide (preferably SnO$_2$). The surface area, determined by the Brunauer-Emmett-Teller (BET) adsorption method employing nitrogen gas, of the solid pretreating composition generally is in the range of from about 50 to about 400 m$^2$/g.

The solid pretreating composition can be prepared by any suitable method. Generally an alumina material having a high surface area (generally at least about 50 m$^2$/g and comprisign less than 10 weight-% of other inorganic refractory materials, e.g., SiO$_2$ or AlPO$_4$) is impregnated with a solution of a suitable dissolved tin compound, followed by drying, and calcining, i.e., heating under such conditions as to substantially convert the tin compound used in the impregnation step to tin oxide. Suitable tin compounds used in the impregnation step include tin(II) chloride, tin(IV) sulfate, tin(II) carboxylates (e.g., acetate), sodium hydroxostannate, tetraalkyltin compounds (preferably tetra-n-butyltin, more preferably dissolved in n-hexane), and the like. Drying of the impregnated alumina material is carried out at conventional conditions (e.g., at about 100°–120° C. in air). Calcining of the dried, impregnated alumina material is carried out at any conditions suitable for converting the tin compound to tin oxide (preferably SnO$_2$), such as by heating at a temperature in the range of from about 200° to about 700° C., for about 1 to about 20 hours, preferably in a free oxygen containing gas atmosphere (preferably air at atmospheric pressure). The pretreating composition can possess any suitable shape, such as spherical, cylinderical, granular, trilobal and the like.

Any suitable contacting conditions can be employed in the pretreating step of this invention, such as those described in U.S. Pat. No. 4,293,728, the disclosure of which is herein incorporated by reference. The pretreatment step can be carried out in any suitable apparatus in any suitable manner. Preferably, the isomerizable monoolefin feed is passed through a fixed bed containing the solid pretreating composition (preferably, tin oxide on alumina material). Generally, the pretreating step is carried out at about 50°–200° C. and at a pressure of about 1–100 atm. Alternatively, a moving bed or a fluidizing bed operation can be employed. The feed can be gaseous or liquid under the pretreating conditions. When the feed is liquid, its flow rate (liquid hourly space velocity) is about 1–10 cc feed per cc per pretreating composition per hour. The solid pretreating composition of this invention can be mixed with other contact materials (such as alumina, silica gel, clay, glass beads, activated carbon), or the fixed bed can contain a layer of the pretreating composition, followed by one or more layers of other contacting materials, including the isomerization catalyst.

The effluent of the pretreatment zone is passed into the isomerization zone (isomerization reactor) where at least a portion of the monoolefin having a terminal double bond (e.g., butene-1) is converted to a monoolefin having an internal double bond (e.g., butene-2). Suitable isomerization catalysts containing a Group VIII noble metal (i.e., at least one metal selected from the group consisting of Ru, Rh, Pd, Os, Ir and Pt) and isomerization conditions are well known and have been described in the patent literature, such as in U.S. Pat. No. 4,293,728, cited above. Presently preferred in particular for the isomerization of butene-1, is an alumina-supported palladium catalyst containing about 0.01 to about 1.0 weight-% Pd, having a surface area (determined by N$_2$ adsorption in accordance with the BET method) in excess of about 200 m$^2$/g. Preferably, isomerization conditions comprise the presence of hydrogen, a temperature of about 40°–150° C., and a pressure of about 1–100 atm (preferably 5–50 atm.) In a continuous operation, generally the liquid hourly space velocity of the feed is in the range of from about 1 to about 10 cc feed/cc catalyst/hour, and the gas hourly space velocity of the hydrogen gas is in the range of from about 5 to about 100 cc H$_2$/cc catalyst/hour. Pretreating and isomerization condition are generally optimized by those skilled in the art so as to maximize the life of the isomerization catalyst and the conversion of the monoolefin having a terminal double bond to at least one monoolefin having an internal double bond.

It is understood that the solid contacting material is discarded and replaced by fresh material when it fails to remove sufficient amounts of impurities (in particular sulfur impurities) from the feed such as to provide a satisfactory monoolefin conversion in the subsequent isomerization step. It is feasible to regenerate spent solid pretreatment material such as by heating in air under conditions as to oxidize and otherwise remove absorbed impurities from the pretreatment material.

The following examples are presented to further illustrate the invention and are not to be construed as unduly limiting the scope of the invention.

EXAMPLE I

This example illustrates the preparation of alumina-based pretreatment materials.

Material A (Control) was spherical alumina having an average particle diameter of 1/32 inch, a surface area (measured by nitrogen adsorption in accordance with the BET method) of 325 m$^2$/g, and a pore volume (measured by mercury porosimetry) of about 0.50 cc/g. Material A was provided by Aluminum Company of America, Pittsburgh, Pa., and had been calcined in air for 2 hours at 500° C.

Material B (Control) was lead oxide on alumina. It was prepared by pouring a solution of 4.14 grams Pb(NO$_3$)$_2$ in 20 cc water over 24.5 grams of Material A, which had been calcined for 2 hours at 500° C. The mixture of alumina and lead nitrate solution was dried at about 110° C. and then calcined in air for 2 hours at 500° C. 10 cc of Material B contained about 0.005 g-atom of Pb.

Material C (Invention) was prepared by pouring 23 cc of a solution of 4.34 tetra-n-butyltin in n-hexane over 24.5 grams of Material A, which had been calcined in air for 2 hours at 400° C. The mixture of alumina and the tetrabutyltin solution was dried for 1 hour at 93° C. and was then calcined for 2 hours at 500° C. 10 cc of Material C contained about 0.005 g-atom of Sn.

EXAMPLE II

A stainless steel tube of 0.5 inch inner diameter and about 20 inches length was filled (from the bottom up) as follows: a 5″ high bottom layer of inert glass beads, a layer of 10 cc commercial Pd/Al$_2$O$_3$ isomerization catalyst (with 0.3 weight-% Pd; provided by Calsicat, 17107 Gaskell Ave., Eria, Pa. 16503), a layer (guard bed) of 10 cc of Material A or B or C, and a 5″ top layer of glass beads.

A hydrocarbon steam comprising isobutane, butene-1, small amounts of other butenes, butadiene and sulfur impurities (about 40–50 ppm S; probably present as organic di- and trisulfides and free sulfur) and a hydrogen gas stream were simultaneously introduced into the heated fixed bed reactor from the top (such that the mixture passed through the guard bed of Material A or B or C before it passed through the layer of the Pd/Al$_2$O$_3$ catalyst). The feed rate of the hydrocarbon stream was about 60 g per hour, and the hydrogen gas feed rate was about 440 cc per hour. When the two streams passed through the fixed bed reactor, the temperature in the Pd/Al$_2$O$_3$ catalyst layer and in the layer of Material A or B or C was 185°-190° F., and the total pressure (controlled by an exit valve) was about 400 psig. Samples of the reaction product exiting at the bottom were taken at various time intervals and were analyzed by means of a gas chromatograph.

The amounts of unconverted butene-1 present in the product of three test runs (employing Material A, B and C, respectively, as guard bed) are plotted as a function of reaction time in FIG. 1. The curves shown in FIG. 1 clearly show that the catalytic activity of the Pd/Al$_2$O$_3$ isomerization catalyst (as indicated by an increase in the amount of unconverted butene-1) decreased after about 4 hours on stream when Material A (Al$_2$O$_3$) was used as guard bed material, and decreased after about 7 hours on stream when Material B (PbO/Al$_2$O$_3$) was employed as guard bed material. The catalyst activity of the Pd/Al$_2$O$_3$ catalyst, however, remained constant for at least 10 hours when Material C (Sn oxide/Al$_2$O$_3$) was employed as guard bed material.

Reasonable variations, modifications and adaptations for various usages and conditions can be made within the scope of the disclosure and the appended claims, without departing from the scope of this invention.

That which is claimed is:

1. In an isomerization process wherein a feed comprising at least one isomerizable monoolefin having a terminal double bond and containing 4–12 carbon atoms per molecule is contacted with a catalyst composition comprising a Group VIII noble metal, under such isomerization conditions as to produce at least one monoolefin having an internal double bond and wherein the performance of said catalyst composition is adversely affected by impurities contained in said feed, the improvement which comprises pretreating said feed, prior to said contacting with said catalyst composition, with a solid pretreating material comprising at least one tin oxide and an inorganic refractory support material, under such pretreating conditions as to remove at least a portion of said impurities and to enhance the performance of said catalyst composition.

2. A process in accordance with claim 1, wherein said Group VIII noble metal is palladium, and said refractory support material is alumina.

3. A process in accordance with claim 1, wherein said feed comprises at least one substance selected from the group consisting of elemental sulfur, hydrogen sulfide, mercaptans, organic sulfides, organic disulfides, carbonyl sulfide and sulfur oxides.

4. A process for isomerizing butene-1 to butene-2 comprising the steps of:
   (a) passing a feed comprising butene-1 and also impurities, which adversely affect the performance of the catalyst composition used in subsequent step (b), through a zone containing a solid pretreating material comprising of at least one tin oxide and alumina, under such pretreating conditions as to remove at least a portion of said impurities and to enhance the performance of said catalyst composition used in step (b); and
   (b) contacting the effluent from step (a) with a catalyst composition comprising a Group VIII noble metal, under such isomerization conditions as to convert at least a portion of butene-1 contained in said feed to butene-2.

5. A process in accordance with claim 4, wherein said catalyst composition used in step (b) comprises palladium and alumina as support material.

6. A process in accordance with claim 4, wherein said feed comprises at least one substance selected from the group consisting of elemental sulfur, hydrogen sulfide, mercaptans, organic sulfides, organic disulfides, carbonyl sulfide, and sulfur oxides.

7. A process in accordance with claim 4, wherein said impurities are sulfur impurities which are present in said feed at a level of about 1 to about 1,000 ppmw.

8. A process in accordance with claim 4, wherein said solid pretreating material has been preparad by a process comprising the steps of impregnating an alumina material with a suitable, dissolved tin compound, drying the thus impregnated alumina material, and heating the dried, impregnated alumina material under said conditions as to substantially convert said tin compound to tin oxide.

9. A process in accordance with claim 8, wherein said tin oxide is SnO$_2$

10. A process in accordance with claim 4, wherein said solid pretreating material comprises about 1 to about 50 weight percent tin oxide and has a surface area, measured by the BET absorption method employing nitrogen gas, of about 50 to about 500 m$^2$/g.

11. A process in accordance with claim 4, wherein said pretreating conditions comprise a temperature in the range of about 50 to about 200° C., a pressure in the range of about 1 to about 100 atm, and a liquid hourly space velocity of said feed of about 1 to about 10 cc feed per cc solid pretreating material per hour.

12. A process in accordance with claim 4, wherein said isomerization conditions comprise the presence of hydrogen gas, a temperature in the range at from about 40 to about 150° C., a pressure in the range of from about 1 to about 100 atm, and a liquid hourly space velocity of said feed in the range of from about 1 to about 10 cc feed per catalyst composition per hour.

13. A process for isomerizing butene-1 to butene-2 comprising the steps of:
   (a) passing a feed comprising butene-1 and also impurities, which adversely affect the performance of the catalyst composition used in subsequent step (b), through a zone containing a solid pretreating material comprising of at least one tin oxide and alumina, at a temperature in the range of from about 50 to about 200° C., under such pretreating conditions as to remove at least a portion of said impurities and to enhance the performance of said catalyst composition used in step (b); and
   (b) contacting the effluent from step (a) with a catalyst composition comprising a Group VIII noble metal, under such isomerization conditions as to convert at least a portion of butene-1 contained in said feed to butene-2.

14. A process in accordance with claim 13, wherein said catalyst composition used in step (b) comprises palladium and alumina as support material.

15. A process in accordance with claim 13, wherein said feed comprises at least one substance selected from the group consisting of elemental sulfur, hydrogen sulfide, mercaptans, organic sulfides, organic disulfides, carbonyl sulfide,and sulfur oxides.

16. A process in accordance with claim 13, wherein said impurities are sulfur impurities which are present in said feed at a level of about 1 to about 1,000 ppmw.

17. A process in accordance with claim 13, wherein said tin oxide is $SnO_2$.

18. A process in accordance with claim 13, wherein said solid pretreating material comprises about 1 to about 50 weight percent tin oxide and has a surface area, measured by the BET absorption method employing nitrogen gas, of about 50 to about 500 $m^2/g$.

19. A process in accordance with claim 13, wherein said pretreating conditions comprise the presence of hydrogen gas, a pressure in the range of about 1 to about 100 atm, and a liquid houly space velocity of said feed of about 1 to about 10 cc feed per cc solid pretreating material per hour.

20. A process in accordance with claim 13, wherein said isomerization conditions comprise the presence of hydrogen gas, a temperature in the range at from about 40 to about 150° C., a pressure in the range of from about 1 to about 100 atm, and a liquid hourly space velocity of said feed in the range of from about 1 to about 10 cc feed per catalyst composition per hour.

* * * * *